(12) United States Patent
Mehta et al.

(10) Patent No.: US 10,895,524 B2
(45) Date of Patent: Jan. 19, 2021

(54) BIOLOGIC FLUID SAMPLE ANALYSIS CARTRIDGE WITH NON-REFLECTIVE BEADS

(71) Applicant: Abbott Point of Care, Inc., Princeton, NJ (US)

(72) Inventors: Manav Mehta, Plainsboro, NJ (US); Robert Holt, East Stroudsburg, PA (US)

(73) Assignee: Abbott Point of Care, Inc., Princeton, NJ (US)

( * ) Notice: Subject to any disclaimer, the term of this patent is extended or adjusted under 35 U.S.C. 154(b) by 409 days.

(21) Appl. No.: 14/768,680

(22) PCT Filed: Feb. 19, 2014

(86) PCT No.: PCT/US2014/017145
§ 371 (c)(1),
(2) Date: Aug. 18, 2015

(87) PCT Pub. No.: WO2014/130542
PCT Pub. Date: Aug. 28, 2014

(65) Prior Publication Data
US 2016/0003731 A1    Jan. 7, 2016

Related U.S. Application Data

(60) Provisional application No. 61/766,543, filed on Feb. 19, 2013.

(51) Int. Cl.
*G01N 1/28* (2006.01)
*G01N 15/05* (2006.01)
(Continued)

(52) U.S. Cl.
CPC ........... *G01N 21/0303* (2013.01); *B01L 9/52* (2013.01); *G01N 1/28* (2013.01); *G01N 15/05* (2013.01);
(Continued)

(58) Field of Classification Search
None
See application file for complete search history.

(56) References Cited

U.S. PATENT DOCUMENTS 4,950,455 A    8/1990   Smith
5,232,830 A    8/1993   Van Ness
(Continued)

FOREIGN PATENT DOCUMENTS

WO    WO0064492 A1    11/2000

OTHER PUBLICATIONS

CN office action for CN201480012716.1 dated Jun. 29, 2016.
(Continued)

*Primary Examiner* — Neil N Turk
(74) *Attorney, Agent, or Firm* — Getz Balich LLC

(57) ABSTRACT

A biological fluid sample analysis chamber and a method for analyzing a biological fluid sample is provided. The chamber includes a first chamber panel, a second chamber panel, and a plurality of beads disposed between the first chamber panel and the second chamber panel, which beads are configured to not reflect light incident to the beads in an amount that appreciably interferes with a photometric analysis of the biologic fluid.

14 Claims, 3 Drawing Sheets

(51) Int. Cl.
  B01L 9/00   (2006.01)
  G01N 21/03  (2006.01)
  G01N 33/49  (2006.01)
  G01N 21/64  (2006.01)
  G01N 21/59  (2006.01)
  B01L 3/00   (2006.01)
  G01N 35/00  (2006.01)

(52) U.S. Cl.
  CPC ......... G01N 21/59 (2013.01); G01N 21/6428 (2013.01); G01N 33/49 (2013.01); B01L 3/502715 (2013.01); B01L 3/502746 (2013.01); B01L 2300/0822 (2013.01); G01N 2021/0307 (2013.01); G01N 2021/6482 (2013.01); G01N 2035/00158 (2013.01); G01N 2201/064 (2013.01)

(56) References Cited

U.S. PATENT DOCUMENTS

| | | | |
|---|---|---|---|
| 6,154,276 A * | 11/2000 | Mariella, Jr. | G01N 15/1436 356/337 |
| 6,350,613 B1 | 2/2002 | Wardlaw et al. | |
| 2001/0041339 A1 | 11/2001 | Anderson et al. | |
| 2002/0155618 A1 | 10/2002 | O'Hagan | |
| 2005/0214863 A1 | 9/2005 | McDevitt et al. | |
| 2005/0221276 A1 | 10/2005 | Rozakis et al. | |
| 2007/0281311 A1 | 12/2007 | Roth et al. | |
| 2008/0166328 A1 * | 7/2008 | Harmon | C12N 5/0605 424/93.7 |
| 2009/0257632 A1 | 10/2009 | Lalpuria et al. | |
| 2010/0268199 A1 | 10/2010 | Hyde et al. | |
| 2011/0244581 A1 | 10/2011 | Nikonorov et al. | |
| 2011/0256573 A1 | 10/2011 | Davis et al. | |
| 2011/0294198 A1 | 12/2011 | Wardlaw | |
| 2012/0021456 A1 | 1/2012 | Levine et al. | |
| 2012/0080610 A1 | 4/2012 | Blasenheim et al. | |
| 2012/0219457 A1 | 8/2012 | Verrant et al. | |
| 2013/0114075 A1 | 5/2013 | Hukari et al. | |

OTHER PUBLICATIONS

EP search report for EP14754884.6 dated Sep. 28, 2016.
Chinese office action for CN201480012716.1 dated Jul. 3, 2017.
EP search report for EP18248240.6 dated Apr. 23, 2019.

* cited by examiner

US 10,895,524 B2

BIOLOGIC FLUID SAMPLE ANALYSIS CARTRIDGE WITH NON-REFLECTIVE BEADS

The present application claims priority to PCT Patent Appln. No. PCT/US2014/017145 filed Feb. 19, 2014, which is entitled to the benefit of and incorporates by reference essential subject matter disclosed in the U.S. Patent Appln. No. 61/766,543, filed Feb. 19, 2013.

BACKGROUND OF THE INVENTION

1. Technical Field

The present invention relates to apparatus for biologic fluid analyses in general, and to cartridges for acquiring, processing, and containing biologic fluid samples for analysis in particular.

2. Background Information

Historically, biologic fluid samples such as whole blood, urine, cerebrospinal fluid, body cavity fluids, etc. have had their particulate or cellular contents evaluated by smearing a small undiluted amount of the fluid on a slide and evaluating that smear under a microscope. Reasonable results can be gained from such a smear, but the cell integrity, accuracy and reliability of the data depends largely on the technician's experience and technique.

In some instances, constituents within a biological fluid sample can be analyzed using impedance or optical flow cytometry. These techniques evaluate a flow of diluted fluid sample by passing the diluted flow through one or more orifices located relative to an impedance measuring device or an optical imaging device. A disadvantage of these techniques is that they require dilution of the sample, and fluid flow handling apparatus.

Some analysis techniques use an analysis chamber that includes beads; e.g., U.S. Pat. No. 4,950,455 issued to Smith. A problem with such analysis chamber occurs when the sample is photometrically imaged. Light directed toward the sample can reflect and create undesirable results that negatively affect analysis of the sample image.

What is needed is an apparatus for evaluating a sample of a biologic fluid that does not suffer from the problems associated with the prior art.

DISCLOSURE OF THE INVENTION

According to an aspect of the present invention, a biological fluid sample analysis chamber is provided. The chamber includes a first chamber panel, a second chamber panel, and a plurality of beads disposed between the first chamber panel and the second chamber panel, which beads are configured to not reflect light incident to the beads in an amount that appreciably interferes with a photometric analysis of the biologic fluid.

According to another aspect of the present invention, a method of analyzing a biological fluid sample is provided. The method includes the steps of: a) disposing the biologic fluid sample in an analysis chamber configured to hold the sample quiescently; b) creating one or more images of the sample using one or more wavelengths of light incident to the sample quiescently residing within the analysis chamber; wherein the analysis chamber has a first chamber panel, a second chamber panel, and a plurality of beads disposed between the first chamber panel and the second chamber panel, which beads are configured to not reflect the light incident to the beads in an amount that appreciably interferes with a photometric analysis of the biologic fluid; and c) analyzing the sample using at least a portion of the one or more images of the sample.

In an embodiment of the foregoing aspects, the plurality of the beads are configured to absorb the incident light in an amount great enough such that any light incident to the beads that is not absorbed does not appreciably interfere with a photometric analysis of the biologic fluid. As an example of such embodiment, the plurality of beads may have a color that absorbs light.

In another embodiment of the foregoing aspects, or in addition to other embodiments, the plurality of the beads may comprise one or more materials that are non-reflective to the incident light in an amount great enough such that any light incident to the beads that is reflected does not appreciably interfere with a photometric analysis of the biologic fluid.

In another embodiment of the foregoing aspects, or in addition to other embodiments, the plurality of beads may comprise a material that absorbs light in an amount such that light incident to the beads will not reflect off of the beads in an amount that appreciably interferes with a photometric analysis of the biologic fluid. The same material, or a different material, may also quench fluorescent emissions from material disposed within or attached to the beads.

The present invention is described herein in terms of aspects and embodiments of those aspects that include elements or features that may be included with the aspects. The identified embodiments may be included with the aspect of the invention singularly or in combination with any of the other identified embodiments as will be described herein below in the Detailed Description. The features and advantages of the present invention will become apparent in light of the detailed description of the invention provided below, and as illustrated in the accompanying drawings.

DETAILED DESCRIPTION

The present invention is directed toward a method and apparatus for photometric analysis of a biologic fluid sample within an analysis chamber. As will be explained below, the sample residing within the analysis chamber is exposed to light and an analysis of the sample is performed using light transmitted through the sample and/or fluorescing from the sample.

Figure 1:
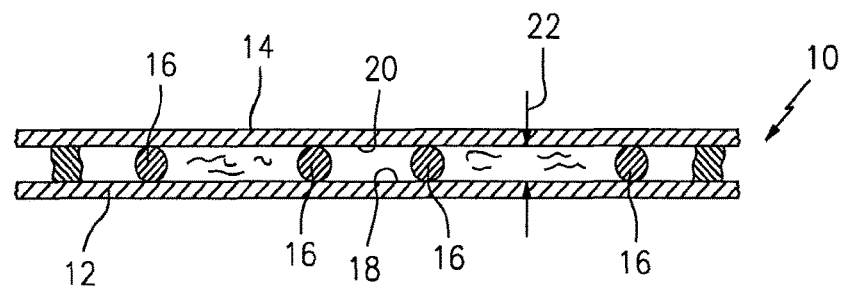
FIG. 1 diagrammatically illustrates an analysis chamber.

Referring to FIG. 1, the analysis chamber 10 is formed by a base chamber panel 12, an upper chamber panel 14, and a plurality of beads 16 disposed there between. At least one of the chamber panels 12, 14 has a transparent region. Preferably, at least a portion of both the base and upper chamber panels 12, 14 are transparent to light (e.g., transparent regions aligned with one another for light transmittance there through). Each chamber panel 12, 14 has an interior surface 18, 20, and an exterior surface 19, 21. When assembled, the interior surfaces 18, 20 of the base chamber panel 12 and the upper chamber panel 14 face toward each other, separated from one another by a distance referred to as the "chamber height" 22. In some embodiments, the interior surfaces 18, 20 are parallel to one another. The present analysis chamber 10 is not, however, limited to a parallel configuration; e.g., the analysis chamber height may vary in regions of the chamber 10, including a sloped configuration, a stepped configuration, etc. In some embodiments, different height (e.g., diameter) beads 16 may used in different regions of the analysis chamber 10.

U.S. patent application Ser. No. 13/341,618 and Ser. No. 13/594,439, both of which are hereby incorporated by reference in their entirety and are commonly assigned with the present application, disclose embodiments of analysis chambers 10 which can be used with the present invention. The present invention is not limited to use with these embodiments, however. In the aforesaid embodiments, the chamber height 22 in at least a portion of the analysis chamber 10 is accurately, uniformly defined by geometric and physical properties of the beads 16 and the chamber panels 12, 14 and is sized to enable capillary forces to draw the sample throughout the chamber 10. In these embodiments, with the exception of a small number of beads 16 that may be substantially undersized, all of the beads 16 are in contact with the interior surfaces 18, 20 of the chamber panels 12, 14.

Examples of acceptable chamber panel materials include transparent plastic film, such as acrylic, polystyrene, polyethylene terphthalate (PET), cyclic olefin polymer (COP), cyclic olefin copolymer (COC), or the like. In those embodiments where the upper chamber panel 14 is designed to flex when subjected to capillary forces, an upper chamber panel 14 made of PET, having a thickness of approximately twenty-three microns (230 provides acceptable flexibility.

The beads 16 preferably are structures independent of both the base chamber panel 12 and the upper chamber panel 14. The beads 16 may be disposed in random distribution with the analysis chamber 10, or in a predetermined arrangement. In some embodiments, an acceptable number of the beads 16 are positioned to an inter-bead spatial density (i.e., distances between adjacent beads 16) sufficient to ensure an acceptably uniform chamber height 22 between the chamber panel interior surfaces 18, 20. In the analysis chamber embodiments disclosed in the aforesaid patent applications, at least one of chamber panels 12, 14 and/or the beads 16 is sufficiently flexible to permit the chamber height 22 to approximate the mean height of the beads 16. The relative flexibility provides an analysis chamber 10 having a substantially uniform height despite the possibility of minor geometric variations in the beads 16 due to manufacturing tolerances of the beads 16. For example, in those embodiments where the beads 16 are relatively flexible, the larger beads 16 compress (as a result of sample fluid exerting capillary forces on the chamber panels) to allow most beads 16 to contact the interior surfaces of both panels, thereby making the chamber height 22 substantially equal to the mean bead diameter. Alternatively, at least one of the chamber panels (e.g., the upper chamber panel 14) may be formed to be as or more flexible than the beads 16. For example, in an embodiment wherein the upper chamber panel 14 is more flexible than the beads 16, the upper chamber panel 14 will overlay the beads 16 and to the extent that a particular bead 16 is larger than the surrounding beads 16, the upper chamber panel 14 will flex around the larger bead 16 in a tent-like fashion; e.g., deflect around the larger bead 16. In this manner, although small local areas of the chamber 10 will deviate from the mean chamber height 22, the mean height of the chamber regions (including the tented areas) will collectively equal the mean bead diameter with a high degree of accuracy. As indicated above, the capillary forces exerted by the sample provide the force necessary to compress the beads 16, or one or both of the chamber panels 12, 14, or some combination thereof. In the above referenced embodiments, when used for analysis of substantially undiluted whole blood, the beads 16 may be polymeric spherical beads 16 that are about four microns (4 μm) in diameter. The present invention is not limited to use with spherical beads 16.

Figure 2:
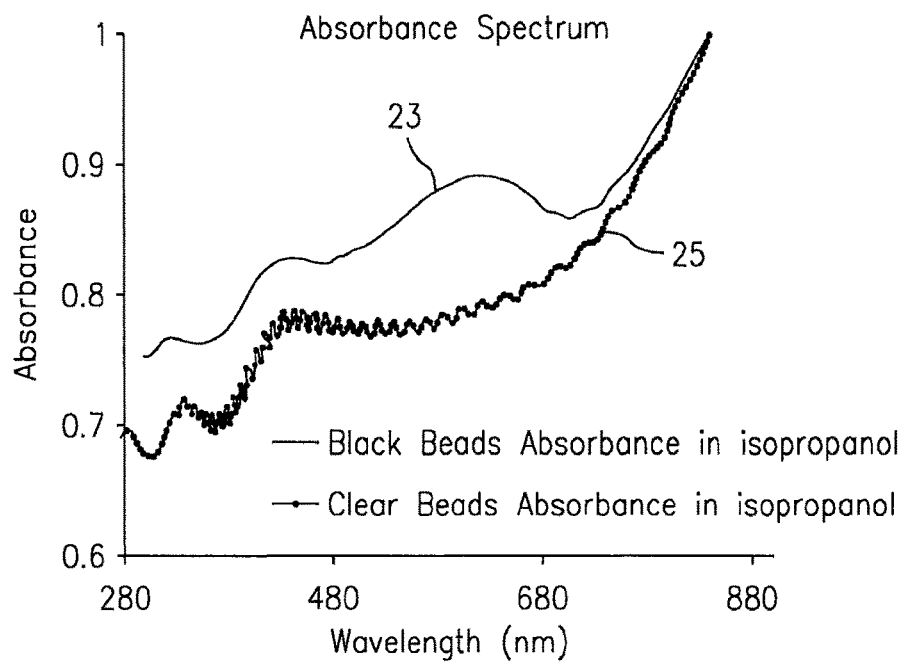
FIG. 2 is a graph of absorbance versus wavelength, diagrammatically illustrating the difference in absorption between black beads and clear beads disposed in isopropanol as a function of light wavelength.

According to an aspect of the present invention, the beads 16 disposed within the chamber 10 are configured to not reflect light incident to the beads (via transmittance or fluorescent emission) at predetermined wavelengths in an amount that appreciably interferes with a photometric analysis of the biologic fluid. As used herein, the term "appreciably" means that to the extent that there is reflection of incident light off a bead 16, if any, the amount of that reflected light is such that the bead 16 is readily distinguishable from constituents within the sample (e.g., platelets, etc). In some embodiments, the configuration of the beads 16 is such that the beads may comprise a material, or include a material on their exterior surface (e.g., a coating), that absorbs incident light at the predetermined wavelengths in an amount great enough such that any incident light that is not absorbed (e.g., light reflected from the bead) does not appreciably interfere with a photometric analysis of the biologic fluid. For example, embodiments of the present invention may use beads 16 having a color (e.g., black) that absorbs incident light at certain wavelengths to a much greater extent than clear or opaque beads 16, or beads 16 having colors more likely to reflect light (e.g., white). FIG. 2 is a graph of absorbance versus wavelength, diagrammatically illustrating the difference in absorption between black beads (line 23) and clear beads (line 25) disposed in isopropanol as a function of light wavelength. As a specific example, black beads 16 will absorb light in the wavelength range of about 400-700 nm. Black is the color that absorbs the most light, but depending upon the photometric analysis application, one or more alternative colors may be used that are operable to absorb incident light at the predetermined wavelengths in an amount great enough such that any incident light that is not absorbed does not appreciably interfere with a photometric analysis of the biologic fluid. In addition, colors that absorb light in the manner described above may be available in different intensities (i.e., shades, tints) that are created by darkening or lightening the pure hue of the color. The "pure hue" of a color is the base color at its full intensity. Consequently, it may be possible to use different intensities of a color, which intensities are operable to absorb incident light at the predetermined wavelengths in an amount great enough such that any incident light that is not absorbed does not appreciably interfere with a photometric analysis of the biologic fluid. The material of the beads 16 may be uniformly colored with the light absorbing color, or the exterior of the beads 16 may have the light absorbing color.

In some embodiments, the beads 16 may be configured with a fluorescence quenching material to create quencher conjugated beads. An example of a material that can be used to create quencher conjugated beads is QSY®7, which is a nonfluorescent acceptor dye available from Molecular Probes, Inc. of Oregon, USA. The present invention is not limited to this particular nonfluorescent acceptor dye, however. It should be noted that some fluorescent quenching materials are also operable to absorb incident light as well.

In some embodiments, the beads 16 may comprise a material, or include a material on their exterior surface (e.g., a coating), that make them sufficiently non-reflective to incident light at the predetermined wavelengths (which is sometimes referred to as "anti-reflective" or "AR") so that any incident light that may be reflected from the bead 16 does not appreciably interfere with a photometric analysis of the biologic fluid. The present invention may also include bead 16 embodiments that use some combination of light absorbing and non-reflective materials, which materials in combination are such that any incident light that may reflect from a bead does not appreciably interfere with a photometric analysis of the biologic fluid.

In some embodiments, the exterior surface 19, 21 of one or both chamber panels 12, 14 may be coated with anti-reflective coating. A non-limiting example of an acceptable anti-reflective coating is FluoroPel™ 601A coating, which is commercially available from Cytonix LLC of Maryland USA.

According to another aspect of the present invention, the beads 16 may be configured to inhibit material attaching to their exterior surface, which material emits fluorescent light when illuminated with excitation light. For example, in analysis applications that use fluorescent dyes, certain dyes may have an affinity for the beads 16 causing them to attach to the beads 16. As a result, incident light at certain wavelengths may cause the dye to fluoresce, and thereby make the beads 16 appear brightly colored. As a specific example, acridine orange (AcO) is a nucleic acid selective fluorescent cationic dye. Beads 16 made of polystyrene are typically negatively charged. As a result AcO particles may have an affinity for the exterior surface of the polystyrene beads 16, and in the presence of light at certain excitation wavelengths can produce fluorescent emission. To decrease or eliminate the affinity between the beads 16 and the dye, the beads 16 may be manufactured and/or modified to have a positive surface charge, which positive charge would have less or no affinity for the positively charged AcO particles. In some embodiments of the present invention, the beads 16 may be both configured to inhibit material that emits fluorescent light when illuminated from attaching to their exterior surfaces, and configured to not reflect light (e.g., include light absorbing materials).

The analysis chambers 10 described above are typically sized to hold about 0.2 to 1.0 μl of sample, but the chamber 10 is not limited to any particular volume capacity, and the capacity can be varied to suit the analysis application. In some embodiments, the chamber 10 is operable to quiescently hold a liquid sample. The term "quiescent" is used to describe that the sample is deposited within the chamber 10 for analysis, and is not purposefully moved during the analysis. To the extent that motion is present within the blood sample residing within the analysis chamber 10 of these embodiments, it will predominantly be due to Brownian motion of the blood sample's formed constituents, which motion is not disabling of the use of this invention. As indicated above, however, the present invention is not limited to these embodiments.

The above described present analysis chamber 10 can be used in a variety of different analysis cartridges and analysis devices. To illustrate the utility of the present analysis chamber 10 and facilitate the description of the present method, a description of an acceptable cartridge and analysis device is provided below. The present analysis chamber 10 is not, however, limited to this specific type of cartridge and/or analysis device.

Figure 3:
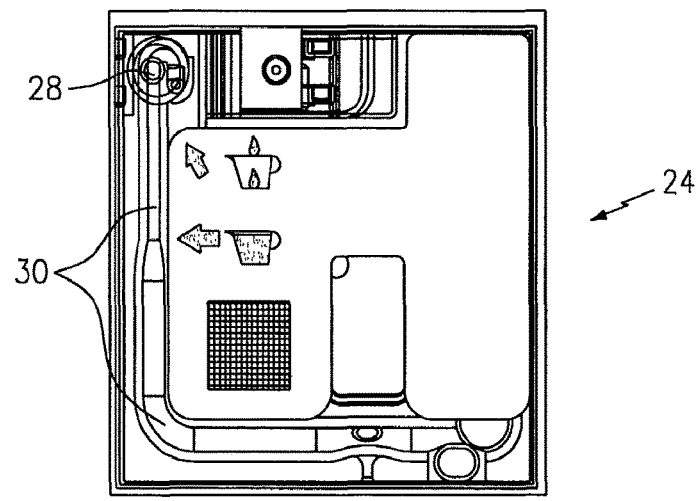
FIG. 3 is a diagrammatic planar view of a cartridge that may be used with the present analysis chamber.

The present analysis chamber 10 may be provided as part of, or with, a cartridge 24 that is configured for use in an automated analysis device 26, wherein a sample disposed within the analysis chamber 10 can be imaged and subsequently analyzed. An example of a cartridge 24 is shown in FIG. 3. U.S. patent application Ser. No. 13/341,618 and Ser. No. 13/594,439, identified and incorporated by reference above, disclose examples of such cartridges 24. The cartridge 24 includes a collection port 28, one or more internal channels 30, and the analysis chamber 10. In FIG. 3, the analysis chamber 10 is disposed internally within the cartridge and therefore may not be visible. The collection port 28 is configured to receive a sample of biologic fluid (e.g., substantially undiluted whole blood) and is in fluid communication with the channels 30. The channels 30, in turn, are in selective fluid communication with the analysis chamber 10. Fluid sample deposited into the collection port 28 may be moved through the channels 30 and into the analysis chamber 10 by a combination of capillary action and motive force produced by a sample motion system; e.g., a fluid actuator. An example of an analysis device 26 with a sample motion system 32 is described in U.S. patent application Ser. No. 13/077,476, which is hereby incorporated by reference in its entirety and is commonly assigned with the present application. The present invention is not limited to using such a system, however.

Figure 4:
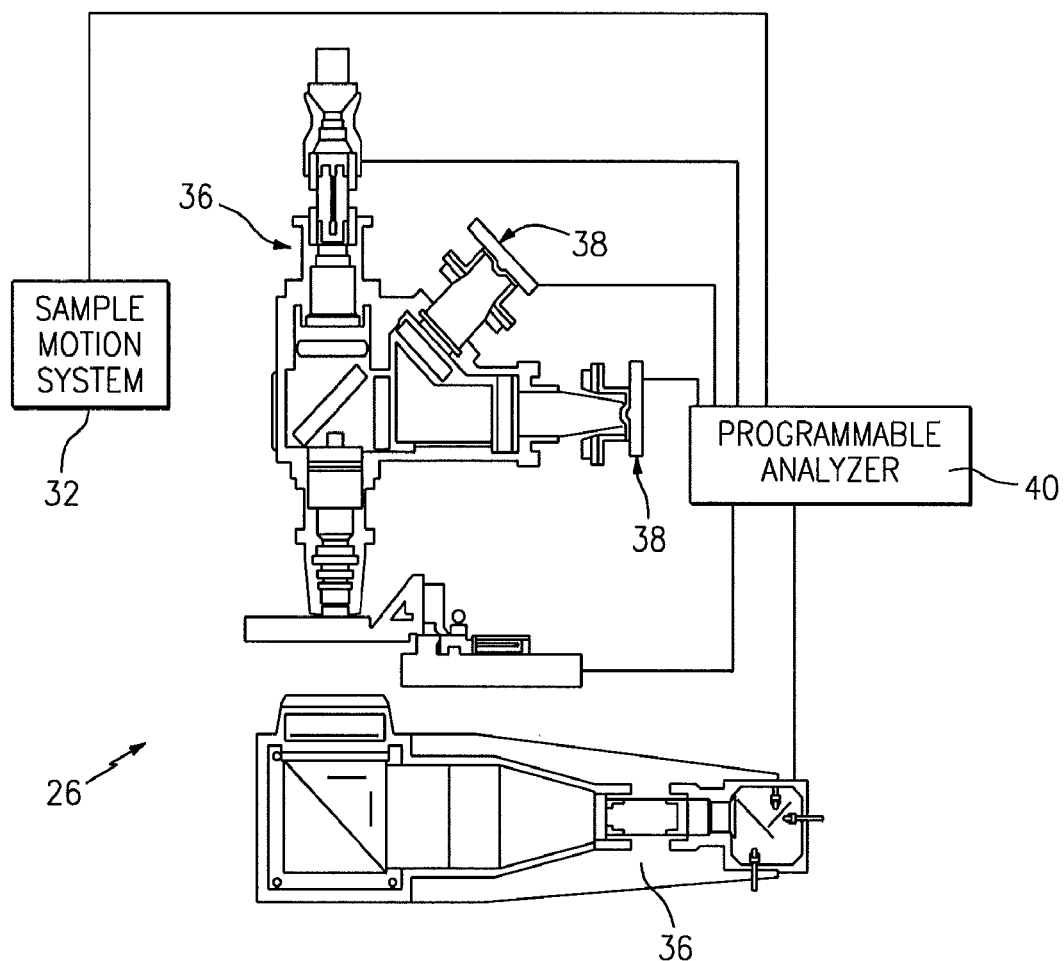
FIG. 4 is a schematic view of an automatic analysis device with which the present analysis chamber may be used.

Now referring to FIG. 4, the analysis device 26 includes a sample objective lens 34, a plurality of sample illuminators 36, at least one image dissector 38, the sample motion system 32, and a programmable analyzer 40. The sample illuminators 36 produce light directed incident to the sample (e.g., in a direction perpendicular to the plane of a chamber panel interior surface 18, 20, of at least one of the chamber panels 12, 14) along predetermined wavelengths. Incident light transmitted through the sample, or light fluoresced from the sample, is captured using one or more image dissectors 38, and a signal representative of the captured light is sent to the programmable analyzer 40, where it is processed into an image. An example of an acceptable image dissector 38 is a charge coupled device (CCD) type image sensor that converts light passing through (or from) the sample into an electronic data format image. Complementary metal oxide semiconductors ("CMOS") type image sensors are another example of an image dissector 38 that can be used.

The programmable analyzer 40 includes a central processing unit or other device operable to carry out functions including: 1) perform the instructions of a computer program: 2) perform basic arithmetical and/or logical functions; and 3), perform input/output operations of the analyzer, etc. The analyzer 40 is in communication with the sample illuminators 36, the image dissector(s) 38, and the sample motion system 32. The analyzer 40 is adapted (e.g., programmed) to receive the signals and selectively perform the functions necessary to operate the sample illuminator(s) 36, the image dissector(s) 38, and the sample motion system 32.

A biologic fluid sample (e.g., a whole blood sample) is deposited directly into an analysis chamber 10, or into a cartridge 24 and is selectively moved through the cartridge 24 (e.g., via a sample motion system 32 and/or capillary action) and into an analysis chamber 10. One or more reagents (e.g., heparin, EDTA, colorant) may be admixed with the sample. In an analysis of a whole blood sample, the addition of one or more reagents relative to the volume of the sample is such that the sample of whole blood will be substantially undiluted.

Now referring to FIG. 4, the analysis device 26 is operable to photometrically image the sample residing within the analysis chamber 10, and subsequently analyze the sample using the image. During imaging, one or more of the sample illuminators 36 are operated to produce light directed incident to the sample at predetermined wavelengths. The incident light may be transmitted through the sample at which point it is captured by an image dissector 38. Transmission light in the range of about 515-700 nm (e.g., red and green light) is useful for analysis of whole blood. The incident light may also be an excitation wavelength that causes fluorescent light emission from a colorant mixed with the sample, which emitted fluorescent light is captured by an image dissector 38. Fluorescent excitation light in the range of about 450-490 nm can be produced by an epi-fluorescent light source. In both instances, a signal representative of the captured light is sent to the programmable analyzer 40, where it is processed into an image.

Figure 5:
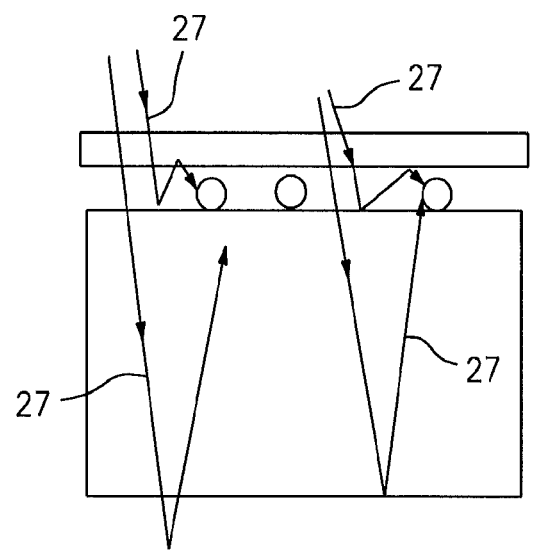
FIG. 5 is a diagrammatic illustration of light reflecting within an analysis chamber.
Figure 6:
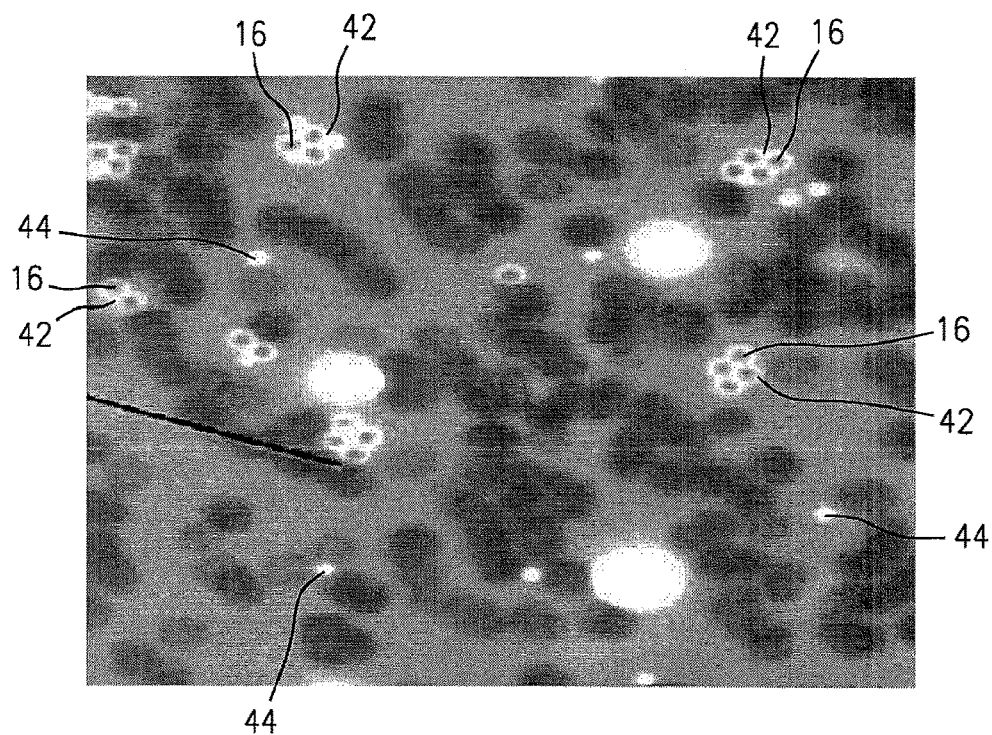
FIG. 6 is an image of a sample quiescently residing within an analysis chamber that includes opaque beads, which image is formed using incident light at 470 nms.

Referring to FIG. 6, an image of a sample quiescently residing within an analysis chamber 10 is shown, which chamber 10 includes a plurality of opaque beads 16 disposed between a pair of parallel chamber panels 12, 14. This image depicts a fluorescent light image created using excitation light at about 470 nm. The opaque beads 16 can be seen within the image, each with a signature ring 42 of relatively bright light caused by light reflecting off of the bead 16. FIG. 5 is a diagrammatic depiction of incident light 27 reflecting off of the various surfaces of the chamber panels 12, 14, illustrating what is believed to be at least a part of the light source reflecting off of the beads and creating the aforesaid signature ring 42. This signature ring 42 can negatively interfere with other analyses of the sample based on this image. For example, platelets 44 within the fluorescent image appear as small regions of bright light. The signature ring 42 of bright light associated with an opaque bead 16 (or other type of bead that similarly reflects light) can be interpreted as one or more platelets 44, or may obscure platelets 44 in close proximity to the bead 16. Consequently, using such beads 16 in this type of photometric analysis can interfere with the analysis of certain constituents within the sample.

Figure 7:
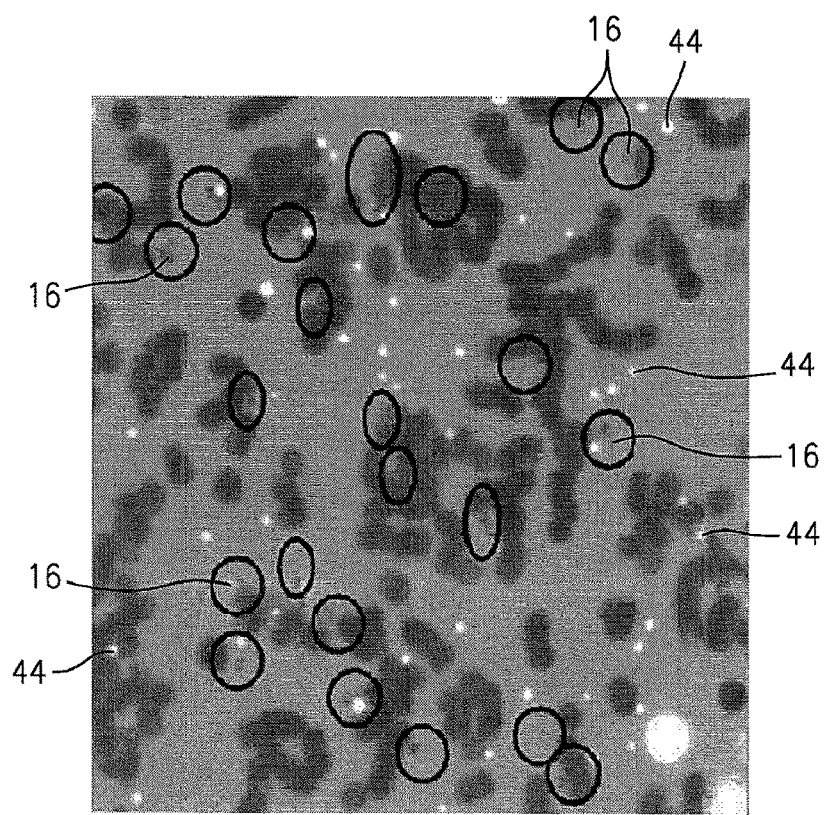
FIG. 7 is an image of a sample quiescently residing within an analysis chamber that includes black colored beads, which image is formed using incident light at 470 nms.

Embodiments of the present invention avoid the photometric interference associated with imaging opaque or clear beads 16 (or other beads 16 that reflect light emitted at predetermined wavelengths—via transmittance or fluorescence—in an amount that appreciably interferes with a photometric analysis of the biologic fluid) by using beads 16 that minimize or eliminate reflected light. For example in some embodiments, the present invention includes using beads 16 comprising a material, or including a material on their exterior surface (e.g., a coating), that make them absorb light at the predetermined wavelengths in an amount great enough such that any light incident to the beads that is not absorbed (e.g., light reflected from the bead 16) does not appreciably interfere with a photometric analysis of the biologic fluid. As a specific example, some embodiments of the present invention use black colored beads 16 that absorb an amount of incident light sufficient to prevent the reflection of light in an amount that will appreciably interfere with a photometric analysis of the biologic fluid. FIG. 7 illustrates a plurality of black colored beads 16 disposed in an analysis chamber 10. The image in FIG. 7 is created using a fluorescent excitation light source at about 463 nm (the present invention is not limited to this using light at this particular wavelength). The signature rings 42 of bright light caused by incident light reflecting off of the beads 16, as shown in FIG. 6, are not present relative to the black beads 16 used in the chamber shown in FIG. 7. In fact, because the black beads 16 have a much less pronounced brightness signature, FIG. 7 shows them encircled with a black oval to facilitate their recognition. Hence, the beads 16 are readily distinguishable from constituents within the sample (e.g., platelets 44) and therefore do not appreciably interfere with the photometric analysis of the sample. In other embodiments, the present invention may utilize beads 16 that comprise a material, or include a material on their exterior surface (e.g., a coating), that make them sufficiently non-reflective to incident light at the predetermined wavelengths so that any incident light that may be reflected from the bead 16 does not appreciably interfere with a photometric analysis of the biologic fluid.

The beads according to the present invention are particularly useful in instances where the analysis involves a sample of whole blood containing white blood cells (WBCs) stained with a fluorescent dye. It is our experience that WBCs, which are substantially larger than platelets and typically larger than the beads, can contain a relatively large amount of the fluorescent dye. When the sample is subjected to an epi-fluorescent light source, the dye within the WBC emits light. Because of the size of the WBC and the amount of dye contained therein, the amount of light emitted from the WBC can be substantial relative to the remainder of the sample; i.e., the WBCs appear bright in the image. If an opaque or clear bead is in close proximity to the WBC, the light emitted from the dye and incident to the adjacent bead can create a significant brightness around the bead as a result of the incident light reflecting off of the bead, which brightness can negatively interfere with the photometric analysis. Using beads according to the present invention, however, minimizes or eliminates the reflection of the incident light and consequently the potential for that reflected light to negatively interfere with the photometric analysis.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention. For example, the present invention is described above using the example of an analysis chamber 10 formed by a pair of chamber panels 12, 14 with beads 16 disposed between and in contact with the interior surfaces 18, 20 of the chamber panels 12, 14. As indicated above, the present invention is not limited to this particular chamber embodiment. The beads 16 may, for example, be disposed between the chamber panels 12, 14 but not in contact with the interior surfaces 18, 20 of the chamber panels 12, 14.

What is claimed is:

1. A method of analyzing a biological fluid sample, comprising:

providing an analysis chamber defined by a first chamber panel having a first interior surface, and a second chamber panel having a second interior surface;

disposing a biologic fluid sample in the analysis chamber, and quiescently holding the fluid sample in the analysis chamber, wherein the biologic fluid sample is mixed with at least one fluorescent dye configured to interact with the biologic fluid sample;

disposing a plurality of beads, each bead having an exterior surface, between the interior surface of the first chamber panel and the interior surface of the second chamber panel, which beads are configured to not reflect light incident to the beads in an amount that appreciably interferes with a photometric analysis of the fluid sample, and wherein each of the beads is configured to inhibit the at least one fluorescent dye from attaching to the exterior surface of that bead;

creating one or more images of the fluid sample using one or more wavelengths of light incident to the fluid sample, while the fluid sample is quiescently residing with the beads within the analysis chamber, and the beads are disposed within the chamber such that the exterior surface of each bead is in direct contact with the fluid sample during the creation of the images; and analyzing the quiescently residing fluid sample using at least a portion of the one or more images of the sample.

2. The method of claim 1, wherein the plurality of beads are configured to absorb the incident light in an amount great enough such that any light incident to the beads that is not absorbed does not appreciably interfere with a photometric analysis of the biologic fluid.

3. The method of claim 2, wherein the plurality of the beads comprises a material that is non-reflective to the incident light in an amount great enough such that any light incident to the beads that is reflected does not appreciably interfere with a photometric analysis of the biologic fluid.

4. The method of claim 2, wherein the plurality of beads comprise a fluorescence quenching material in an amount such that light incident to the beads will not reflect off of the beads in an amount that appreciably interferes with a photometric analysis of the biologic fluid.

5. The method of claim 1, wherein the first chamber panel has an exterior surface, and the second chamber panel has an exterior surface, and an anti-reflective coating is disposed on the exterior surface of the first chamber panel, or on the exterior surface of the second chamber panel, or on both.

6. The method of claim 1, wherein the plurality of beads comprise a polystyrene material.

7. The method of claim 6, wherein the plurality of beads, comprising said polystyrene material, have a positive surface charge.

8. A method of analyzing a biological fluid sample, comprising:

providing an analysis chamber defined by a transparent first chamber panel having a first interior surface, and a transparent second chamber panel having a second interior surface;

disposing the biologic fluid sample in the analysis chamber, and quiescently holding the fluid sample in the analysis chamber;

disposing a plurality of beads, each having an exterior surface, between the interior surface of the first chamber panel and the interior surface of the second chamber panel, which beads are configured to not reflect light incident to the beads in an amount that appreciably interferes with a photometric analysis of the fluid sample;

creating one or more images of the fluid sample by transmitting light at one or more wavelengths of light through the fluid sample while the fluid sample is quiescently residing with the beads within the analysis chamber, and the beads are disposed within the chamber such that the exterior surface of each bead is in direct contact with the fluid sample during the creation of the images, wherein the one or more images are created using a captured portion of the light transmitted through the sample; and analyzing the quiescently residing fluid sample using at least a portion of the one or more images of the sample.

9. The method of claim 8, wherein the plurality of the beads comprises a material that is non-reflective to the incident light in an amount great enough such that any light incident to the beads that is reflected does not appreciably interfere with a photometric analysis of the biologic fluid.

10. The method of claim 8, wherein each bead is configured to inhibit material attaching to the exterior surface of that bead, which material emits fluorescent light when illuminated with excitation light.

11. The method of claim 10, wherein the plurality of beads comprise a polystyrene material.

12. The method of claim 11, wherein the plurality of beads, comprising said polystyrene material, have a positive surface charge.

13. The method of claim 8, wherein the plurality of beads comprise a fluorescence quenching material in an amount such that light incident to the beads will not reflect off of the beads in an amount that appreciably interferes with a photometric analysis of the biologic fluid.

14. The method of claim 8, wherein the first chamber panel has an exterior surface, and the second chamber panel has an exterior surface, and an anti-reflective coating is disposed on the exterior surface of the first chamber panel, or on the exterior surface of the second chamber panel, or on both.

* * * * *